(12) United States Patent
Cole

(10) Patent No.: US 7,663,756 B2
(45) Date of Patent: Feb. 16, 2010

(54) CAVITY ENHANCED PHOTO ACOUSTIC GAS SENSOR

(75) Inventor: Barrett E. Cole, Bloomington, MN (US)

(73) Assignee: Honeywell International Inc, Morristown, NJ (US)

( * ) Notice: Subject to any disclaimer, the term of this patent is extended or adjusted under 35 U.S.C. 154(b) by 0 days.

(21) Appl. No.: 12/176,988

(22) Filed: Jul. 21, 2008

(65) Prior Publication Data

US 2010/0014086 A1 Jan. 21, 2010

(51) Int. Cl.
*G01N 21/00* (2006.01)

(52) U.S. Cl. .................. 356/437; 356/432; 356/440; 356/445; 250/573; 250/576

(58) Field of Classification Search .............. 356/432, 356/436–438, 440–445; 250/573–576
See application file for complete search history.

(56) References Cited

U.S. PATENT DOCUMENTS

| | | | |
|---|---|---|---|
| 4,233,568 A | 11/1980 | Hamerdinger et al. |
| 4,612,647 A | 9/1986 | Norvell |
| 4,614,961 A | 9/1986 | Khan et al. |
| 4,870,224 A | 9/1989 | Smith et al. |
| 4,973,131 A | 11/1990 | Carnes |
| 5,022,745 A | 6/1991 | Zayhowski et al. |
| 5,040,895 A | 8/1991 | Laurent et al. |
| 5,135,304 A | 8/1992 | Miles et al. |
| 5,146,465 A | 9/1992 | Khan et al. |
| 5,278,435 A | 1/1994 | Van Hove et al. |
| 5,311,280 A | 5/1994 | Koper et al. |
| 5,408,319 A | 4/1995 | Halbout et al. |
| 5,418,868 A | 5/1995 | Cohen et al. |
| 5,450,053 A | 9/1995 | Wood |
| 5,468,910 A | 11/1995 | Knapp et al. |

(Continued)

FOREIGN PATENT DOCUMENTS

DE 3311808 10/1984

(Continued)

OTHER PUBLICATIONS

Gillis et al., "Photoacoustic Spectroscopy for Quantitation of Trace Gases in Air," Chemical Science and Technology Laboratory National Institute of Standards and Technology, Industrial and Analytical Instruments and Services Forensics and Homeland Security, 2 pages, prior to Jul. 21, 2008.

(Continued)

*Primary Examiner*—Gregory J Toatley, Jr.
*Assistant Examiner*—Iyabo S Alli
(74) *Attorney, Agent, or Firm*—Kris T. Fredrick

(57) ABSTRACT

Devices and method for photo acoustically detecting a gas are disclosed. In one illustrative embodiment, a gas sensor includes an optical cavity defined by one or more optical segments separating at least two mirrors. A photo acoustic cell, configured to receive a gas from the surrounding environment, is provided at least partially within one or more of the optical segments of the optical cavity. One of the at least two mirrors is configured to couple electromagnetic radiation into the optical cavity and to interact with the gas. A detector is acoustically coupled to the photo acoustic cell to detect absorption of the electromagnetic radiation by the gas.

20 Claims, 2 Drawing Sheets

U.S. PATENT DOCUMENTS

Figure 1:
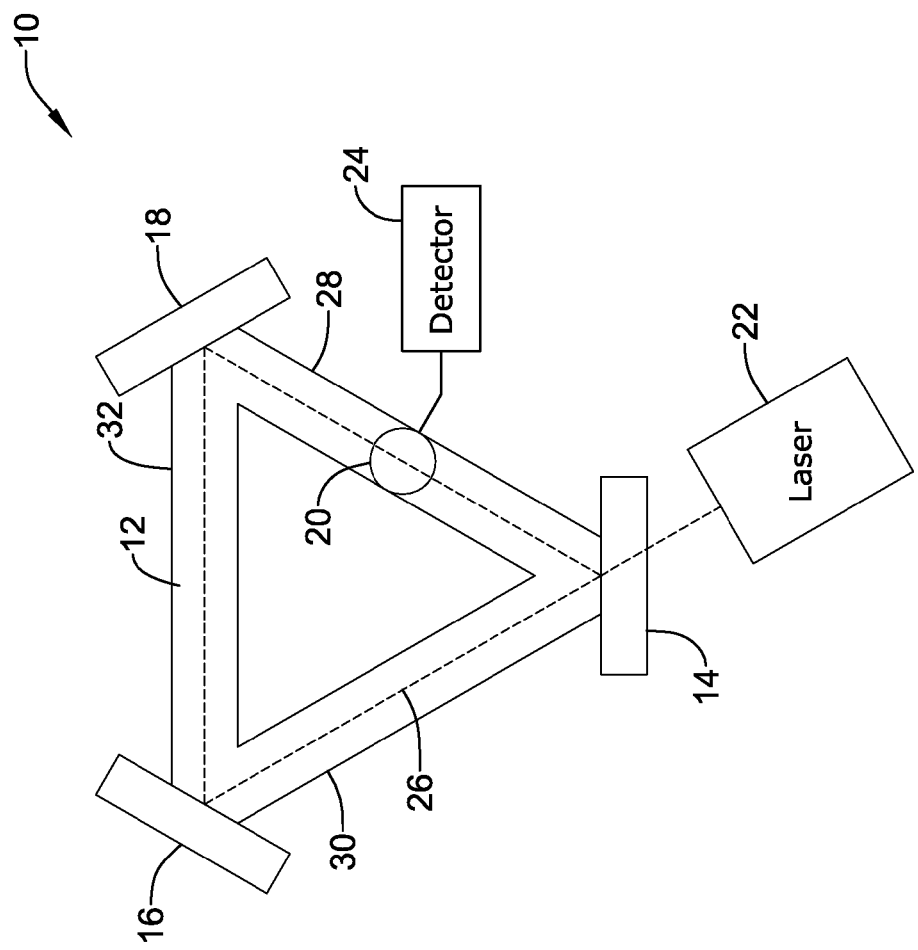

| | | | |
|---|---|---|---|
| 5,512,750 A | 4/1996 | Yanka et al. | |
| 5,528,040 A | 6/1996 | Lemann | |
| 5,550,373 A | 8/1996 | Cole et al. | |
| 5,629,951 A | 5/1997 | Chang-Hasnain et al. | |
| 5,677,538 A | 10/1997 | Moustakas et al. | |
| 5,679,965 A | 10/1997 | Schetzina | |
| 5,723,706 A | 3/1998 | Brasier et al. | |
| 5,739,554 A | 4/1998 | Edmond et al. | |
| 5,815,277 A | 9/1998 | Zare et al. | |
| 5,832,017 A | 11/1998 | Ramdani et al. | |
| 5,834,331 A | 11/1998 | Razeghi | |
| 5,847,397 A | 12/1998 | Moustakas | |
| 5,869,896 A | 2/1999 | Baker et al. | |
| 5,900,650 A | 5/1999 | Nitta | |
| 5,909,280 A | 6/1999 | Zavracky | |
| 5,912,740 A | 6/1999 | Zare et al. | |
| 5,915,051 A | 6/1999 | Damask et al. | |
| 5,933,565 A | 8/1999 | Diebold | |
| 5,960,025 A | 9/1999 | Thorland et al. | |
| 6,040,895 A | 3/2000 | Haas | |
| 6,080,988 A | 6/2000 | Ishizuya et al. | |
| 6,084,682 A | 7/2000 | Zare et al. | |
| 6,091,504 A | 7/2000 | Walker et al. | |
| 6,115,122 A | 9/2000 | Bao et al. | |
| 6,122,416 A | 9/2000 | Ooba et al. | |
| 6,147,756 A | 11/2000 | Zavracky et al. | |
| 6,208,798 B1 | 3/2001 | Morozov et al. | |
| 6,287,940 B1 | 9/2001 | Cole et al. | |
| 6,295,130 B1 | 9/2001 | Sun et al. | |
| 6,296,779 B1 | 10/2001 | Clark et al. | |
| 6,310,904 B1 | 10/2001 | Thorland et al. | |
| 6,324,192 B1 | 11/2001 | Tayebati | |
| 6,335,669 B1 | 1/2002 | Miyazaki et al. | |
| 6,380,531 B1 | 4/2002 | Sugihwo et al. | |
| 6,384,953 B1 | 5/2002 | Russell et al. | |
| 6,404,648 B1 | 6/2002 | Slupe et al. | |
| 6,406,578 B1 | 6/2002 | Schober et al. | |
| 6,421,127 B1 | 7/2002 | McAndrew et al. | |
| 6,438,149 B1 | 8/2002 | Tayebati et al. | |
| 6,452,680 B1 | 9/2002 | Paldus et al. | |
| 6,483,130 B1 | 11/2002 | Yang et al. | |
| 6,492,726 B1 | 12/2002 | Quek et al. | |
| 6,507,107 B2 | 1/2003 | Vaiyapuri | |
| 6,545,739 B1 | 4/2003 | Matsumoto et al. | |
| 6,583,917 B2 | 6/2003 | Melloni et al. | |
| 6,584,126 B2 | 6/2003 | Wang et al. | |
| 6,590,710 B2 | 7/2003 | Hara et al. | |
| 6,594,059 B2 | 7/2003 | Flanders | |
| 6,597,713 B2 | 7/2003 | Ouchi | |
| 6,608,711 B2 | 8/2003 | Flanders et al. | |
| 6,627,983 B2 | 9/2003 | Tu et al. | |
| 6,658,034 B2 | 12/2003 | Garnache et al. | |
| 6,670,599 B2 | 12/2003 | Wagner et al. | |
| 6,728,286 B2 | 4/2004 | Thorland et al. | |
| 6,816,636 B2 | 11/2004 | Cole et al. | |
| 6,836,501 B2 | 12/2004 | Cox et al. | |
| 6,879,014 B2 | 4/2005 | Wagner et al. | |
| 6,985,281 B2 | 1/2006 | Wagner et al. | |
| 7,002,697 B2 | 2/2006 | Domash et al. | |
| 7,012,696 B2 | 3/2006 | Orr et al. | |
| 7,015,457 B2 | 3/2006 | Cole et al. | |
| 7,046,362 B2 | 5/2006 | Lehmann et al. | |
| 7,049,004 B2 | 5/2006 | Domash et al. | |
| 7,089,781 B2 | 8/2006 | Petrovic et al. | |
| 7,106,763 B2 | 9/2006 | Tan et al. | |
| 7,113,256 B2 | 9/2006 | Butler et al. | |
| 7,145,165 B2 * | 12/2006 | Cox et al. | 356/442 |
| 7,147,165 B2 | 12/2006 | Mongin et al. | |
| 7,147,695 B2 | 12/2006 | Mitra | |
| 7,221,827 B2 | 5/2007 | Domash et al. | |
| 7,263,871 B2 * | 9/2007 | Selker et al. | 73/24.02 |
| 7,304,799 B2 | 12/2007 | Ma et al. | |
| 7,369,242 B2 | 5/2008 | Cole et al. | |
| 2002/0191268 A1 | 12/2002 | Seeser et al. | |
| 2004/0234198 A1 | 11/2004 | Wagner et al. | |
| 2004/0255853 A1 | 12/2004 | Ma et al. | |
| 2005/0030628 A1 | 2/2005 | Wagner et al. | |
| 2005/0082480 A1 | 4/2005 | Wagner et al. | |
| 2005/0105184 A1 | 5/2005 | Ma et al. | |
| 2005/0254056 A1 | 11/2005 | Kachanov et al. | |
| 2007/0133001 A1 | 6/2007 | Cox et al. | |
| 2008/0151248 A1 | 6/2008 | Cole et al. | |

FOREIGN PATENT DOCUMENTS

| | | |
|---|---|---|
| DE | 19635421 | 12/1997 |
| EP | 0177918 | 3/1991 |
| EP | 0667548 | 1/1995 |
| EP | 1069658 | 1/2001 |
| EP | 1061618 | 11/2007 |
| JP | 03252172 | 11/1991 |
| JP | 05095130 | 4/1993 |
| JP | 7288334 | 10/1995 |
| WO | 9326049 | 12/1993 |
| WO | 9942875 | 8/1999 |

OTHER PUBLICATIONS

Siegman, "Lasers, Chapter 11: Laser Mirrors and Regenerative Feedback," 5 pages, 1986.

Bernstein et al., "Development of a Miniature Silicon PhotoAcoustic Gas Sensor", Presented at Opto 96, Leipzig, Germany, 6 pages, Sep. 26-29, 1999.

Brown, et al., "Visible-Blind UV Digital Camera Based on a 32*32 Array of GAN/AlGAN P-I-N Photodiodes", MRS Internet Journal of Nitride Semiconductor Research, vol. 4S1, pp. 1-10, Sep. 1999.

Campargue et al., "Measurement of SiH2 Density in a Discharge by Intracavity Laser Absorption Spectroscopy and CW Cavity Ring-Down Spectroscopy," Journal of Physics D. Applied Physics, vol. 31, No. 10 pp. 1168-1175, May 21, 1998.

Chitica et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.

Chou et al., "Diode-Laser Measurements of He-, Ar-, and N2-Broadened HF Lineshapes in the First Overtone Band," Journal of Molecular Spectroscopy 196, pp. 70-76, 1999.

Chung et al., "Design and Fabrication of 10×10 Micro-Spatial Light Modulator Array for Phase and Amplitude Modulation," Sensors and Actuators, vol. 78, No. 1, pp. 63-70, Jan. 1999.

Cole et al., "Microscopic Spectroscopy of Optical MEMS Devices," Topic 2 (Materials and Technology), Honeywell Laboratories, 2 pages, on or Around Dec. 11, 2000.

Edwards, "Multiple-Traverse Absorption Cell Design," Journal of the Optical Society of America, vol. 51, No. 1, pp. 98-102, Jan. 1961.

Ferber et al., "A Miniature Silicon Photoacoustic Detector for Gas Monitoring Applications", presented at the MTEX International Conference on Sensors and Transducers, Birmingham, UK, 7 pages, Feb. 14, 2001.

Jerman et al., "A Miniature Fabry-Perot Interferometer with a Corrugated Silicon Diaphragm Support," Sensors and Actuators, vol. A29, No. 2, pp. 151-158, Nov. 1991.

Kurochkin et al., "Complex-Cavity Two-Mode CO2 Laser for Saturated Intracavity Absorption Spectroscopy," Optical Spectroscopy, vol. 68, No. 6, pp. 793-797, 1990.

Kurochkin et al., "Three-Mirror Cavity CO2 Laser for Intracavity Saturated-Absorption Spectroscopy," Optical Spectroscopy, vol. 65, No. 2, pp. 265-267, 1988.

O'Keefe et al., "Cavity Ring-Down Optical Spectrometer for Absorption Measurements Using Pulsed Laser Sources," Review of Scientific Instruments, 59, 11 pages, 1988.

Paul et al., "Cavity Ringdown Measures Trace Concentrations," Laser Focus World, pp. 71-80, Mar. 1997.

Richman et al., "Continuously Tunable, Single-Longitudinal-Mode, Pulsed Mid-Infrared Optical Parametric Oscillator Based on Periodically Poled Lithium Niobate," Optical Society of America, vol. 17, No. 7, pp. 1233-1239.

Sadeghi et al., "Cavity Ring Down Spectroscopy Applied to Plasma Diagnostics," Proc. Int. Symp. Laser-aided Plasma Diagnostics Lake Tahoe, CA, , 8 pages, Sep. 1999.

Scherer et al., "Infrared Cavity Ringdown Laser Absorption Spectroscopy (IR-CRLAS) in Low Pressure Flames," Applied Physics B., vol. 64, pp. 699-705, 1997.

Schweber, "An Old Communications Problem Reoccurs in Optical-Communication-System Design—How it Works: Making the Laser Diode Tunable", EDN, 3 pages, Sep. 28, 2000.

Shimizu et al., "Stark Spectroscopy by 10μ Lasers Using a Multipath Cell," Journal of Applied Physics, vol. 46, No. 1, pp. 258-259, Jan. 1975.

Smirnov et al., "Dye Lasers Using a Three-Mirror Cavity with Lamp Excitation," 4 pages, 1981.

Spence et al., "A Laser-Locked Cavity Ring-Down Spectrometer Employing an Analog Detection Scheme," Review of Scientific Instruments, vol. 71, No. 2, pp. 347-353, Feb. 2000.

Sze, "Physics of Semiconductor Devices." pp. 763-765, John Wiley & Sons, N.Y., 1982.

Tayebati et al., "Microelectromechanical Tunable Filter with Stable Half Symmetric Cavity," Electronics Letters, IEE Stevanage, GB, vol. 34, No. 20, pp. 1967-1968, Oct. 1998.

Tayebati et. al., "Widely Tunable Fabry-Perot Filters Using High Index-Contrast DBRs," Design and Manufacturing of WDM Devices, Dallas, Texas, Nov. 4-5, 1997, SPIE vol. 3234, pp. 206-218, 1998.

Yang et al., "Back-Illuminated GAN/AlGAN Heterojunction Photodiodes With High Quantum Efficiency and Low Noise," Applied Physics Letters, vol. 73, No. 8, pp. 1086-1088, XP000777678, Aug. 24, 1998.

\* cited by examiner

CAVITY ENHANCED PHOTO ACOUSTIC GAS SENSOR

FIELD

The present invention relates generally to gas sensors, and more particularly, to high sensitivity gas sensors.

BACKGROUND

Gas sensors are widely used in many diverse applications, including commercial applications, military applications, and private applications. The sensitivity of such gas sensors can vary, and the type of gas sensor used for a particular application is often selected depending on the required sensitivity. In some applications, it may be desirable to detect gas concentrations as low as a few parts per billion, or even less. Many commercially available gas sensors do not have a high enough sensitivity to detect these and other gas concentrations.

SUMMARY

The following summary is provided to facilitate an understanding of some of the innovative features unique to the present invention and is not intended to be a full description. A full appreciation of the invention can be gained by taking the entire specification, claims, drawings, and abstract as a whole.

This disclosure relates generally to gas sensors, and more particularly, to high sensitivity gas sensors. In one illustrative embodiment, a cavity enhanced photo acoustic gas sensor is provided that includes an optical cavity defined by two or more optical segments separating at least two mirrors. A photo acoustic cell configured to receive a gas sample is provided within one or more of the optical segments of the optical cavity. At least one of the at least two mirrors may couple electromagnetic radiation light from electromagnetic radiation source such as laser into the optical cavity, and the admitted light beam may be significantly amplified by the optical cavity and allowed to interact with the gas sample.

The admitted light beam is at least partially absorbed by the gas sample when the wavelength of the light beam is at or near an absorption line of a gas in the gas sample. The amount of absorption may be dependent on the concentration of the gas in the gas sample. In some cases, the electromagnetic radiation source may be tunable to different wavelengths to help identify a particular gas species in the gas sample.

The gas sensor may include a detector acoustically coupled to the photo acoustic cell to detect the interaction of the electromagnetic radiation and the gas. The detector may be, for example, a microphone or any other suitable sensor that is capable of detecting an acoustic signal (e.g. pressure pulse) that is emitted by the interaction of the electromagnetic radiation and the gas. In some cases, light from the electromagnetic radiation source may be prevented from entering the optical cavity, sometimes periodically, and the ring down time decay of the light in the optical cavity may be used to help sense the gas concentration within the gas sample. The ring down time decay may be dependent on the absorption of the electromagnetic radiation by the gas in the photo acoustic cell.

BRIEF DESCRIPTION

Figure 2:
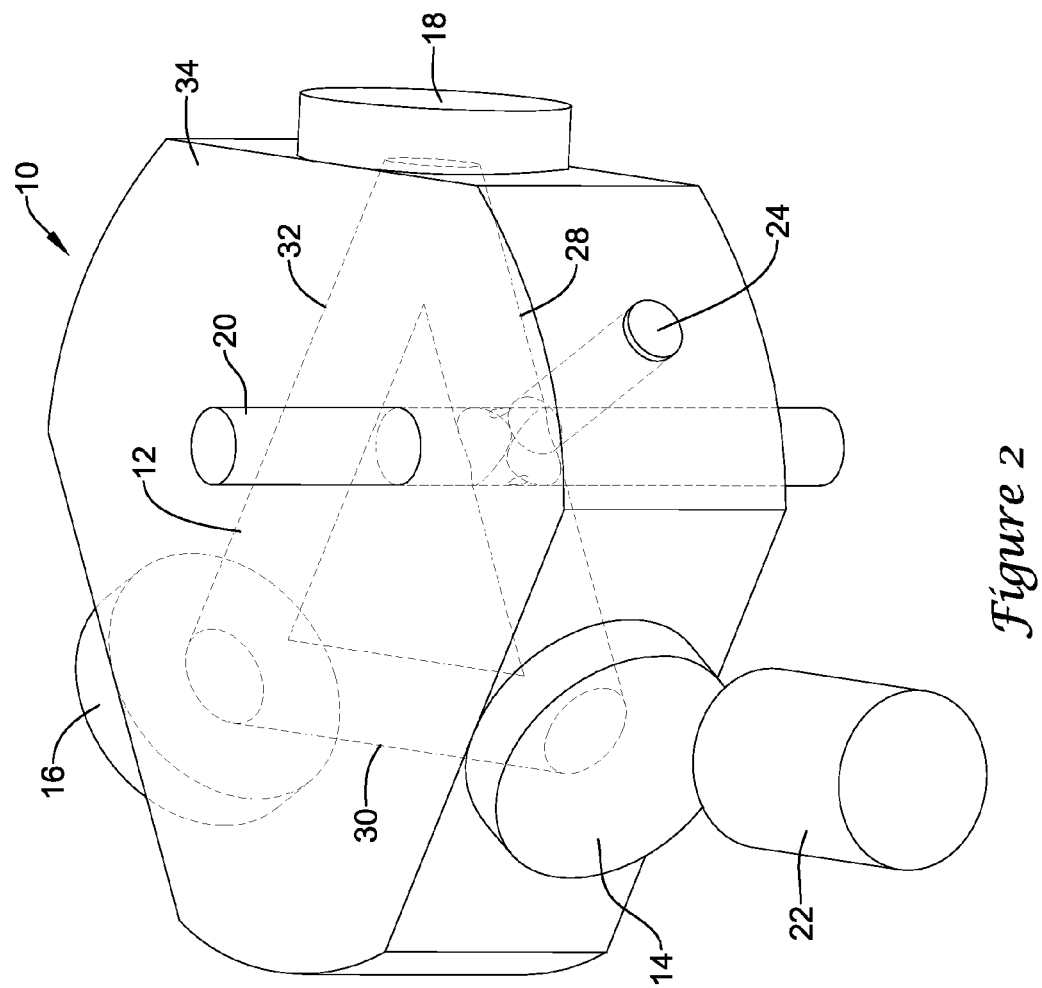

The invention may be more completely understood in consideration of the following detailed description of various illustrative embodiments of the invention in connection with the accompanying drawings, in which:

FIG. 1 is a schematic diagram of an illustrative photo acoustic gas detection system; and FIG. 2 is a perspective view of the illustrative photo acoustic gas detection system of FIG. 1.

DESCRIPTION

The following description should be read with reference to the drawings wherein like reference numerals indicate like elements throughout the several views. The detailed description and drawings show several embodiments which are meant to be illustrative of the claimed invention.

FIG. 1 is a schematic diagram of an illustrative photo acoustic gas detection system 10. The illustrative photo acoustic gas detection system 10 may provide a highly sensitive gas sensor that can be used to detect low concentrations of gas in an environment. In some cases, the photo acoustic gas detection system 10 may be capable of detecting gas concentrations as low as a few parts per billion, a few parts per trillion, or even a few parts per quadrillion, as desired.

In the illustrative embodiment, the gas detection system 10 may include an electromagnetic radiation source such as a laser, an optical cavity 12, a photo acoustic cell 20 configured to receive a gas sample, and a detector 24 to detect the interaction (e.g. absorption) of the electromagnetic radiation beam with the gas sample. The illustrative electromagnetic radiation source 22, which in some cases may be a laser, LED or any other suitable light source, may be configured to emit a beam of electromagnetic radiation, such as beam 26. In some embodiments, the beam 26 may be emitted by a coherent light source such as a laser 22. While not required, the laser may be tunable to different wavelengths, which may be useful to help identify a particular gas species in the gas sample. When so provided, the light beam 26 may be tuned to a high absorption line, or wavelength close thereto, of a gas to be detected. In some cases, the laser 22 may be an IR tunable input laser that is tunable in or around the infrared band.

Alternatively, a laser 22 having a fixed wavelength (i.e. non-tunable) may be used. In this case, the laser 22 may be selected to have a wavelength that is close to or at a high absorption line of a gas species to be detected. Quantum cascade lasers may be suitable, but not required. Some example lasers that may be suitable include, for example, lasers available from New Focus™, such as the Velocity Product line, Telecom, or Daylight Solutions, such as a 4.5 micron laser model number TLS-21045 or a Chiller Model 1001 having a model number TLS-21045. However, the wavelength of the laser to be used depends on the absorption spectra of the gas sample. While lasers are used as one example, this is not meant to be limiting in any manner, and it is contemplated that any suitable electromagnetic radiation source may be used, as desired.

In the illustrative embodiment of FIG. 1, the optical cavity 12 has three linear optical segments 28, 30, and 32 arranged to define a triangular-shaped optical path for the optical cavity 12. In this illustrative embodiment, the optical cavity 12 includes three mirrors 14, 16, and 18 arranged so as to permit a light beam 26 to travel in a continuous path around the optical cavity 12. As illustrated, mirrors 14, 16, and 18 are disposed in each of three corners of the optical cavity 12. As shown, mirror 14 intersects optical linear segment 28 and optical linear segment 30, mirror 16 intersects optical linear segment 30 and optical linear segment 32, and mirror 18 intersects optical linear segment 32 and optical linear segment 28 of optical cavity 12. While three mirrors are shown in the illustrative embodiment of FIG. 1, it is contemplated that more or less mirrors may be used, as desired. For example, it is contemplated that two mirrors that causes a light beam to travel back and forth between the two mirrors can be used, if desired.

In the illustrative embodiment of FIG. 1, mirrors 14 and 16 may be passive mirrors, and mirror 18 may be an active mirror. In some cases, active mirror 18 may be deformable or otherwise actuatable, and passive mirrors 14 and 16 may be non-deformable. For example, passive mirrors 14 and 16 may be dielectric mirrors. In one illustrative embodiment, dielectric mirrors 14 and 16 may be configured to have a relatively high reflectivity on the internal surface and to at least partially transparent on the external surface. The relatively high reflectivity on the internal surface of dielectric mirror 14 and 16 may help to reflect light within the optical cavity 12 to reduce loss. The at least partial transparency on the external surface of, for example, mirror 14, may help incident light beam 26 pass through mirror 14 and enter the optical cavity 12.

Active mirror 18 may be mechanically and/or electrically deformable or otherwise actuatable so as to move the optical cavity 12 in and out of resonance at the wavelength of the electromagnetic radiation source 22. In some cases, the active mirror 18 may be a piezoelectric mirror 18. Piezoelectric mirror 18 may be configured to deform when an electrical potential is applied across a piezoelectric element of the mirror 18. For example, an applied electrical potential may cause at least a portion of the mirror to expand and/or contract. In one example, the center of the piezoelectric mirror 18 may move in and out in response to the applied electrical potential, causing the focal length of the mirror 18 to change. In some embodiments, the electrical potential may oscillate, causing the piezoelectric mirror 18 to deform at a frequency of the applied oscillating electrical potential. The frequency that the active mirror 18 oscillates may dictate an acoustic chopping frequency at which light pulses are periodically applied to the gas sample in the photo acoustic cell 20.

In some cases, the piezoelectric mirror 18 may be configured to deform around one or more node positions. The one or more node positions may be positions of the piezoelectric mirror 18 in which the optical cavity 12 may have a resonance condition. Accordingly, the oscillation of the piezoelectric mirror 18 may cause the optical cavity 12 to move in and out of the resonance condition at the oscillating frequency of the piezoelectric mirror 18. In some cases, the resonance condition may occur twice for each oscillation cycle of the mirror 18, but could be more or less depending on the resonance conditions of the optical cavity 12. In one example, the oscillating frequency of the piezoelectric mirror 18 may be such that the resonance condition of the optical cavity 12 occurs on the order of milliseconds, however, any suitable time period may be used. Similar to mirrors 14 and 16, piezoelectric mirror 18 may be configured to have a relatively high reflectivity on the internal surface to reduce loss, and in some cases, be at least partially transparent on the external surface.

In the illustrative embodiment of FIG. 1, passive mirror 14 is an entrance mirror for the optical cavity 12, or more specifically, the mirror in which the beam 26 passes through to enter the optical cavity 12. It is contemplated, however, that passive mirror 16 or active mirror 18 may be the entrance mirror for the cavity 12, if desired. When the optical cavity 12 is in a resonance condition, the beam 26 that is coupled into the optical cavity 12 via passive mirror 14 may be amplified as the beam travels around and around the optical cavity. This amplification may help increasing the sensitivity of the detection of gas in the photo acoustic cell 20. In some cases, the amplification of the beam 26 may be on the order of 100 times to 1000 times or more relative to the amplitude of the light beam emitted by light source 22. When the active mirror 16 cause the optical cavity 12 to fall out of resonance, the light beam traveling around the optical cavity 12 is stored for a period of time, typically on the order of microseconds, but decays with a ring down time. The ring down time decay will be dependent on the absorption of the light beam 26 by the gas in the photo acoustic cell 20.

In the illustrative embodiment of FIG. 1, the photo acoustic cell 20 is positioned in line with at least one of the optical segments 28, 30, and 32. In the illustrative embodiment, the photo acoustic cell 20 is positioned in line with optical segment 28. In the illustrative embodiment, the photo acoustic cell 20 may include a channel having a first end and a second end with an intermediate portion of the channel configured to intersect the optical path of the cavity 12. The first end and/or the second end may be exposed to the surrounding environment to receive a gas sample. The intermediate portion of the channel may allow the beam 26 to interact with the gas sample. In some cases, the intermediate portion of the channel of the photo acoustic cell 20 may have a pair of openings or windows configured to pass the light beam 26 to the gas sample. These windows should be mounted at Brewster's angle so that the window surface reflections are zero and the cavity light can have maximum intensity. In some cases, the photo acoustic cell 20 may be the only portion of the optical cavity 12 having the gas sample therein, but this is not required.

A detector 24 may be configured to detect the interaction (e.g. absorption) of the light beam 26 with the gas sample in the photo acoustic cell 20. In some cases, the detector 24 may be an acoustic detector, such as a microphone or other transducer, that is configured to detect an acoustic signal such as one or more pressure pulses created by the absorption of the light beam 26 by the gas sample. In some cases, the detector 24 may produce a zero measurement when no gas is detected in the photo acoustic cell 20 (i.e. no gas is present that has an absorption line at or near the wavelength of the light source 22).

In operation, the optical cavity 12 may couple in light beam 26 via mirror 14. When the optical cavity 12 is in a resonance condition, according to the current state of the active mirror 18, the light beam 26 is amplified and interacts with the gas sample in the photo acoustic cell 20. Detector 24 then detects a pressure pulse or other acoustical signal that is related to the absorption of the light beam 26 by the gas sample. The wavelength of the light beam 26 may help specify the gas species that is detected. As such, and in some embodiments, the wavelength of the light beam 26 may be tuned by the light source 22 to correspond to an absorption line of a particular gas species to be detected.

In some cases, the ring-down time of the optical cavity (i.e. time for absorption of the beam 26 by the gas) may be on the order of micro-seconds, such as, for example, 10 micro-seconds, depending on the concentration and/or degree of absorption by the gas. In some cases, the ring down time may be monitored to obtain a measure of the gas concentration in the gas sample, if desired.

In some embodiments, the photo acoustic gas detection system 10 may include an optical detector (not shown) configured to detect a portion of the light beam 26 that may leak out of mirrors 14, 16, and/or 18. The intensity of the light beam 26 detected by the optical detector may be compared to an intensity of the light beam 26 before it enters the optical cavity 12 via mirror 14. The comparison of the intensities of the beam of light 26 may be used to normalize the photo acoustic cell 20 (i.e. adjust for noise) for the intensity of the beam of light 26, but this is not required.

FIG. 2 is a perspective view of the illustrative photo acoustic gas detection system 10 of FIG. 1. As illustrated, the optical cavity 12 is provided in a housing 34 defining the optical segments 28, 30, and 32. The ends of optical segments 28, 30, and 32 may intersect mirrors 14, 16, and 18, which are disposed about the side surfaces of the housing 34. In some cases, the photo acoustic cell 20 may be a generally tubular member including a first end and a second end exposed to the environment surrounding the gas sensor assembly 10. As illustrated, the photo acoustic cell 20 may be disposed through at least a portion of housing 34 to intersect optical linear segment 28. In some cases, detector 24 may be at least partially disposed within or outside of housing 34, and may be in acoustic communication with the photo acoustic cell 20 to detect the interaction (e.g. absorption) of the gas with the light beam 26. In some cases, Brewster angle windows (not shown) may be provided in the housing to help protect the mirrors 14, 16, and 18 from being exposed to and/or contaminated by the gas sample in the photo acoustic cell 20 and/or the external environment in general, but this is not required.

It should be understood that the above-described optical cavity 12 is exemplary and that the optical cavity 12 can take on any form that permits an incoming light beam 26 to be introduced into the cavity 12, travel around and be amplified by the cavity 12, and allows direct or indirect measurement of the amount of gas in the photo acoustic cell 20 disposed in the cavity 12.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respect, only illustrative. Changes may be made in details, particularly in matters of shape, size, and arrangement of parts without exceeding the scope of the invention. The invention's scope is, of course, defined in the language in which the appended claims are expressed.

The invention claimed is:

1. A gas sensor comprising: an electromagnetic radiation source configured to emit a beam of light;
   an optical cavity defined by three or more optical segments separating at least two mirrors, the at least two mirrors being configured to reflect the beam of light through the three or more optical segments, wherein one of the at least two mirrors is an entrance mirror configured to couple at least a portion of the beam of light from the electromagnetic radiation source into the optical cavity;
   a photo acoustic cell provided at least partially in one or more of the optical segments of the optical cavity, the photo acoustic cell configured to receive a gas and contain the gas so as to prevent the at least two mirrors from being exposed to the gas; and
   a detector acoustically coupled to the photo acoustic cell, the detector configured to detect an acoustic signal that is related to the absorption of the beam of light by the gas in the photo acoustic cell.

2. The gas sensor of claim 1 wherein the beam of light is tuned to an absorption line of the gas.

3. The gas sensor of claim 1 wherein one of the at least two mirrors is electrically deformable.

4. The gas sensor of claim 3 wherein the one of the at least two mirrors that is electrically deformable deforms around at least one node position according to an applied electrical potential.

5. The gas sensor of claim 3 wherein the one of the at least two mirrors that is electrically deformable is a piezoelectric mirror.

6. The gas sensor of claim 4 wherein the at least one node position of the one of the at least two mirrors that is electrically deformable provides a resonance condition in the optical cavity.

7. The gas sensor of claim 6 wherein the rate of time that the one of the at least two mirrors that is electrically deformable moves in and out of the at least one node position is a first period of time.

8. The gas sensor of claim 7 wherein the absorption of the beam of light by the gas creates one or more pressure pulses in the photo acoustic cell, and wherein the detector is an acoustical detector that detects the one or more pressure pulses.

9. The gas sensor of claim 7 wherein the time that it takes the gas to absorb the beam of light after the one of the at least two mirrors that is electrically deformable deforms moves the optical cavity out of resonance is a second period of time, the second period of time being less than the first period of time.

10. A photo acoustic gas sensor comprising: a laser configured to emit a beam of light having a wavelength corresponding to an absorption wavelength of a gas to be detected;
    an optical cavity including at least two mirrors separated by three or more optical segments, wherein one of the at least two mirrors couples the beam of light from the laser into the optical cavity, wherein one of the at least two mirrors is electrically tunable to move the optical cavity in and out of a resonance condition, wherein the one of the at least two mirrors that is electrically tunable is configured to deform the mirror around at least one node position according to an applied electrical signal;
    a photo acoustic cell disposed at least partially within one or more of the optical segments of the optical cavity, the photo acoustic cell configured to receive the gas to be detected; and
    an acoustical detector acoustically coupled to the photo acoustic cell to detect the interaction of the beam of light and the gas.

11. The gas sensor of claim 10 wherein the at least one node position of the one of the at least two mirrors provides the resonance condition in the optical cavity.

12. The gas sensor of claim 11 wherein the one of the at least two mirrors that is electrically tunable moves in and out of the at least one node position at a first period of time.

13. The gas sensor of claim 10 wherein the interaction of the beam of light and the gas is an absorption of the beam of light by the gas that creates one or more pressure pulses in the photo acoustic cell.

14. The gas sensor of claim 13 wherein the acoustical detector detects the one or more pressure pulses in the photo acoustic cell.

15. A method of photo acoustically detecting a gas, the method comprising:
    activating a laser to provide a light beam having a wavelength corresponding to an absorption line of a gas;
    transmitting the light beam into an optical cavity via one of at least two mirrors, wherein the optical cavity includes the at least two mirrors separated by three or more optical segments, wherein one of the at least two mirrors is electrically deformable according to an applied electrical signal;

providing a gas in a photo acoustic cell, wherein the photo acoustic cell intersects one or more of the optical segments; and detecting an absorption of the laser beam by the gas in the photo acoustic cell with an acoustical detector.

16. The method of claim 15 wherein the one of the at least two mirrors that is electrically deformable has a node position providing a resonance condition in the optical cavity.

17. The method of claim 16 further comprising moving the one of the at least two mirrors that is electrically deformable in and out of the node position at a rate of time causing the optical cavity to move in and out of the resonance condition at the rate of time.

18. The gas sensor of claim 10 wherein the deformation of the one of the at least two mirrors that is electrically tunable changes the focal length of the one of the at least two mirrors that is electrically tunable.

19. The gas sensor of claim 1 wherein the beam of light has a first intensity when the beam of light is emitted from the electromagnetic radiation source, the first intensity may be compared to a second intensity of the beam of light that exits the optical cavity through one of the at least three mirror to normalize the photo acoustic cell to the first intensity of the beam of light.

20. The gas sensor of claim 10 wherein the one of the at least two mirrors that is electrically tunable is a piezoelectric mirror.

* * * * *